United States Patent
Noguchi et al.

(10) Patent No.: US 6,400,454 B1
(45) Date of Patent: Jun. 4, 2002

(54) APPARATUS AND METHOD FOR INSPECTOR DEFECTS

(75) Inventors: Minori Noguchi, Mitsukaido; Shunji Maeda, Yokohama; Yukihiro Shibata, Fujisawa; Takanori Ninomiya, Hiratsuka, all of (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 09/490,844

(22) Filed: Jan. 24, 2000

(30) Foreign Application Priority Data

Jan. 27, 1999 (JP) .......................... 11-019035

(51) Int. Cl.$^7$ .............................................. G01N 21/89
(52) U.S. Cl. .................................. 356/237.3; 356/237.4
(58) Field of Search ........................... 356/237.1, 237.2, 356/237.3, 237.4, 237.5, 237.6, 394, 600; 250/559.45, 559.06, 559.22

(56) References Cited

U.S. PATENT DOCUMENTS

| | | | | |
|---|---|---|---|---|
| 5,274,343 A | * | 12/1993 | Morioka et al. | 356/237 |
| 5,463,459 A | * | 10/1995 | Morioka et al. | 356/237 |
| 5,473,426 A | * | 12/1995 | Hayano et al. | 356/237 |
| 5,663,569 A | * | 9/1997 | Hayano | 250/559.45 |
| 5,739,526 A | * | 4/1998 | Furstenau et al. | 250/227.14 |
| 5,774,222 A | * | 6/1998 | Maeda et al. | 356/394 |
| 6,084,671 A | * | 7/2000 | Holcomb | 356/354 |
| 2001/0008447 A1 | * | 7/2001 | Nikoonahad et al. | 356/237.2 |

FOREIGN PATENT DOCUMENTS

JP         362044714      *   2/1987

* cited by examiner

Primary Examiner—Hoa Q. Pham
(74) Attorney, Agent, or Firm—Antonelli, Terry, Stout & Kraus, LLP

(57) ABSTRACT

The present invention provides a defect inspection method and an apparatus adopting the method which comprises the steps of:

using a radiation optical system to radiate a Gaussian light beam to an area of detection on a substrate serving as an object of inspection and having a circuit pattern created thereon wherein the Gaussian light beam is shaped to give an illumination-intensity distribution of a Gaussian distribution having a standard deviation about equal to the distance from an optical axis of the area of detection to the periphery of the area of detection;

using a detection optical system to form an optical image of the area of detection on the substrate serving as an object of inspection by radiation of the shaped Gaussian light beam to a photo-sensitive surface of a detector corresponding to the area of detection and to detect a picture signal corresponding to the area of detection and originating from the detector; and detecting a defect caused by typically an extraneous material existing in the area of detection on the basis of the detected picture signal.

20 Claims, 11 Drawing Sheets

SURFACE-RADIATION
TDI IMAGE SENSOR

BACK-PLANE-RADIATION
TDI IMAGE SENSOR (TDI : Time Delay & Integration)

APPARATUS AND METHOD FOR INSPECTOR DEFECTS

BACKGROUND OF THE INVENTION

The present invention relates to a defect testing apparatus and a defect testing method for inspecting a state of generation of defects such as foreign particles in a fabrication process such as a semiconductor fabrication process, a liquid-crystal-display fabrication process and a print-board fabrication process wherein a defect such as a foreign particle generated in a process to create a pattern on a substrate to produce an object is detected and analyzed in order to determine a countermeasure.

In the conventional semiconductor fabrication method, a foreign particle existing on a semiconductor substrate also known as a wafer causes a defect such as poor insulation of a wire or a short circuit. Furthermore, in the case of a miniaturized semiconductor device, an infinitesimal foreign particle existing in a semiconductor substrate results in poor insulation of a capacitor or destruction of typically a gate oxide film. These foreign particles are introduced to get mixed with a semiconductor material in a variety of states due to a variety of causes. For example, a foreign particle is generated by a movable part of a transportation apparatus or a human body. A foreign particle can also be generated as a result of a chemical reaction in processing equipment using a process gas or mixed with chemicals or a raw material.

Likewise, if a foreign particle is introduced to get mixed with a pattern, causing some defects in a process to fabricate a liquid-crystal display device, the resulting display device is not usable. The process to fabricate a print board is in the same situation. That is to say, a mixed foreign particle causes a poor connection and a short circuit in a pattern.

Prior arts related to apparatuses and methods for detecting defects such as foreign particles are disclosed in Japanese Patent Laid-open No. Hei 1-250847, Japanese Patent Laid-open No. Hei 6-258239, Japanese Patent Laid-open No. Hei 6-324003, Japanese Patent Laid-open No. Hei 8-210989 and Japanese Patent Laid-open No. Hei 8-271437 and referred to as prior arts 1, 2, 3, 4 and 5 respectively.

In prior art 1, there is described an inspection apparatus for inspecting surface characteristics of a substrate. The inspection apparatus includes a storage means for storing desired surface characteristics of the substrate, a radiation means for radiating a beam to an area on the surface of the substrate to be inspected all but uniformly, a TDI image sensor means for forming an image of the area on the surface of the substrate to which the beam is radiated by the radiation means, and a comparison means for comparing the image of the area on the surface of the substrate formed by the TDI image sensor means with the desired surface characteristics of the substrate stored in the storage means.

In prior art 2, there is described a defect inspecting apparatus comprising a conveyance means for conveying a substrate having repetitive patterns with different pitches, a radiation means for forming a plane-wave beam into a straight line and radiating the plane-wave beam to the substrate, a space filter, a detector for detecting an optical image formed by an image formation optical system and supplied to the detector through the space filter, elimination means for comparing signals, which are generated to represent the repetitive patterns with large pitches on the substrate and supplied to the elimination means through the space filter for an elimination purpose, with each other, and a defect detection means for detecting a defect caused by typically a very small extraneous material existing on the substrate on the basis of a signal generated by the elimination means.

In prior art 3, there is described a defect inspecting apparatus comprising a detection head, a pitch detection means, an operator processing system, an extraneous-material data memory, a large-extraneous-material data memory, a pattern memory, a software processing system, a parameter transfer means, an extraneous-material memory, a coordinate-data creation means and a microcomputer wherein the detection head includes a radiation means, a detection optical system, a space-filter unit, a detector, an operational amplifier and an A/D converter.

In prior art 4, there is described a very-small-defect detecting apparatus for detecting a-very smell defect caused by typically a very small extraneous material having a size in a range of 0.3$\mu$m to 0.8 $\mu$m or smaller and existing on a substrate by splitting a laser beam emitted from a semiconductor laser oscillator into a plurality of optical beams not interfering each other so as to make intensities of beams reflected by a thin film created on the substrate smooth or uniform, converging the optical beams and radiating the converged optical beams at effectively the same time to the thin film passing the beams at different incidence angles T1 to Tn, converging lights scattered by a very small defect by using a light converging lens, and detecting the converged lights by using a detector such as a TDI image sensor.

In prior art 5, there is described an extraneous-material inspecting apparatus comprising a radiation optical system for radiating a beam generated by a light source to a sample comprising repetitive chips, a detection optical system including a linear image sensor for receiving lights reflected and scattered by the sample and for converting the reflected and scattered lights into a signal, and an interchip comparison means for comparing signals output by the linear image sensor employed in the detection optical system for the repetitive chips in order to detect a comparison mismatch as existence of an extraneous material on the sample, wherein the radiation optical system includes, a shading correction plate having a plurality of curved transmission portions created thereon for an intensity distribution of the beam generated by the light source to correct the beam radiation so as to give an all but equal phase distribution in the straight-line transversal direction and an all but uniform radiation intensity in the straight-line longitudinal direction, and a light converging subsystem for converging the radiated beam and radiating the converged beam to the sample in a slanting direction with respect to the surface of the sample.

In the prior arts described above, however, it is not easy to detect a defect cause by a very small extraneous material with a size of about 0.1 $\mu$m or smaller existing on a substrate, on which repetitive patterns coexist with non-repetitive patterns, with a high degree of sensitivity and at a high speed.

This is because, with the prior arts described above, the farther the distance from a location in an inspected area to the optical axis of the detection optical system, the lower the MTF (Modulation Transfer Function) for the location so that the illumination intensity of the radiated light in regions surrounding the inspected area is not sufficient, making it difficult to inspect a defect with a high degree of sensitivity and at a high speed.

SUMMARY OF THE INVENTION

It is thus an object of the present invention addressing the problems described above to provide a defect inspecting apparatus and a defect inspection method that are capable of inspecting an area of inspection also for a defect caused by typically a very small extraneous material having a size of about 0.1 μm or smaller with a high degree of sensitivity and at a high speed by effectively utilizing the light quantity of a Gaussian optical beam emitted by an ordinary low-cost light source.

It is another object of the present invention to provide a defect inspecting apparatus and a defect-inspection method that are capable of inspecting an area of inspection also for a defect caused by typically a very small extraneous material having a size of about 0.1 μm or smaller by employing a TDI image sensor for receiving an optical image based on a DUV (Distant Ultra Violet) laser beam obtained from a substrate being inspected.

It is a further object of the present invention to provide a defect inspecting apparatus and a defect inspection method that are capable of inspecting an area of inspection also for a defect caused by typically a very small extraneous material having a size of about 0.1 μm or smaller with a high degree of sensitivity and at a high speed by effectively utilizing the light quantity of a beam emitted by a lamp serving as a light source and by solving the problem of an insufficient illumination intensity in regions surrounding an area of detection on a substrate serving as an object of inspection with the insufficient illumination intensity caused by the fact that, the farther the distance from a region to the optical axis of the detection optical system, the lower the MTF for the region.

It is a still further object of the present invention to provide a defect inspecting apparatus and a defect inspection method that are capable of inspecting an area of inspection also for a defect caused by typically a very small extraneous material having a size of about 0.1 μm or smaller with a high degree of sensitivity and at a high speed by effectively utilizing the light quantity of a Gaussian optical beam emitted by an ordinary low-cost light source and by solving the problem of an insufficient illumination intensity in regions surrounding an area of detection on a substrate serving as an object of inspection with the insufficient illumination intensity caused by the fact that, the farther the distance from a region to the optical axis of the detection optical system, the lower the MTF for the region.

In order to achieve the objects described above, the present invention is characterized in that, in an area with a minimum illumination intensity in an illumination-intensity distribution within a radiation range, radiation of a beam is implemented to give a maximum illumination intensity and the S/N ratio of a signal representing a detected beam is maximized in order to improve the detection sensitivity and to increase the throughput.

That is to say, the present invention is characterized in that, by radiating a Gaussian optical beam to an area of detection on a substrate serving as an object of inspection with the Gaussian optical beam shaped to provide a maximum illumination intensity on the outermost circumference (or the periphery) of the area of detection, the sensitivity (the S/N ratio) on the outermost circumference in a detector can be increased and a defect caused by typically a very small extraneous material existing in the area of detection can be detected with a high degree of sensitivity and at a high speed. It should be noted that, by a maximum illumination intensity, an illumination intensity of about 60% of the illumination intensity at the center of the area of detection is meant.

In addition, the present invention also provides a defect inspection method and an apparatus adopting the method comprising the steps of:

using a radiation optical system including a radiation light source to radiate a Gaussian light beam to an area of detection on a substrate serving as an object of inspection and having a circuit pattern created thereon wherein the Gaussian light beam is shaped to give an illumination-intensity distribution of a Gaussian distribution having a standard deviation about equal to the distance from the optical axis of the area of detection to the periphery of the area of detection;

using a detection optical system to form an optical image of the area of detection on the substrate serving as an object of inspection by radiation of the shaped Gaussian light beam to a photo-sensitive surface of a detector corresponding to the area of detection;

detecting a picture signal corresponding to the area of detection and originating from the detector; and detecting a defect caused by typically an extraneous material existing in the area of detection on the basis of the detected picture signal.

Furthermore, the present invention also provides a defect inspection method and an apparatus adopting the method comprising the steps of:

using a radiation optical system to radiate a Gaussian light beam to an area of detection on a substrate serving as an object of inspection and having a circuit pattern created thereon wherein the Gaussian light beam is shaped by adaptation of the diameter or the longitudinal length of the beam to the distance between peripheries having the optical axis of the area of detection as the center thereof so that the ratio of the illumination intensity on the peripheries of the area of detection to the illumination intensity at the center of the area of detection is in a range of about 0.46 to about 0.73 or, ideally, in a range of about 0.54 to about 0.67;

using a detection optical system to form an optical image of the area of detection on the substrate serving as an object of inspection by radiation of the shaped Gaussian light beam to a photo-sensitive surface of a detector corresponding to the area of detection;

detecting a picture signal corresponding to the area of detection and originating from the detector; and detecting a defect caused by typically an extraneous material existing in the area of detection on the basis of the detected picture signal.

Moreover, in the defect inspection method and the apparatus adopting the method provided by the present invention, the Gaussian light beam has a slit shape and the substrate serving as an object of inspection is moved relatively to the Gaussian light beam with a slit shape in a direction crossing the longitudinal direction of the Gaussian light beam.

Further, in the defect inspection method and the apparatus adopting the method provided by the present invention, the detector is a TDI image sensor.

In addition, in the defect inspection method and the apparatus adopting the method provided by the present invention, the shaped Gaussian light beam is radiated to the area of radiation on the substrate serving as an object of inspection in a slanting direction with respect to the surface of the area.

Furthermore, the present invention also provides a defect inspection method and an apparatus adopting the method comprising the steps of:

using a radiation optical system to radiate a Gaussian light beam to an area of detection on a substrate serving as an object of inspection and having a circuit pattern created thereon wherein the Gaussian light beam is shaped wherein the Gaussian light beam is shaped by adaptation of the diameter or the longitudinal length of the beam to the distance between peripheries having the optical axis of the area of detection as the center thereof so that the ratio of the illumination intensity on the peripheries of the area of detection to the illumination intensity at the center of the area of detection is in a range of about 0.46 to about 0.73 or, ideally, in a range of about 0.54 to about 0.67;

using a detection optical system to form an optical image of the area of detection on the substrate serving as an object of inspection by radiation of the shaped Gaussian light beam to a photo-sensitive surface of a detector corresponding to the area of detection;

detecting a picture signal corresponding to the area of detection and originating from the detector; and detecting a defect caused by typically an extraneous material existing in the area of detection on the basis of the detected picture signal.

Moreover, the present invention also provides a defect inspection method and an apparatus adopting the method comprising the steps of:

using a radiation optical system to radiate a DUV beam to an area of detection on a substrate serving as an object of inspection and having a circuit pattern created thereon;

using a detection optical system to form an optical image of the area of detection on the substrate serving as an object of inspection by radiation of the shaped DUV beam on a DUV-light-sensitive surface of a TDI image sensor corresponding to the area of detection;

detecting a picture signal corresponding to the area of detection and originating from the TDI image sensor; and detecting a defect caused by typically an extraneous material existing in the area of detection on the basis of the detected picture signal.

Further, the present invention also provides a defect inspection method and an apparatus adopting the method comprising the steps of:

using a radiation optical system to radiate a DUV beam to an area of detection on a substrate serving as an object of inspection and having a circuit pattern created thereon wherein the DUV beam is shaped to give an illumination-intensity distribution of a Gaussian distribution having a standard deviation about equal to the distance from the optical axis of the area of detection to the periphery of the area of detection;

using a detection optical system to form an optical image of the area of detection on the substrate serving as an object of inspection by radiation of the shaped DUV beam on a DUV-light-sensitive surface of a TDI image sensor corresponding to the area of detection;

detecting a picture signal corresponding to the area of detection and originating from the TDI image sensor; and detecting a defect caused by typically an extraneous material existing in the area of detection on the basis of the detected picture signal.

According to a configuration described above, a problem of an insufficient illumination intensity on the periphery of an area of detection on a substrate serving as an object of inspection caused by the fact that, the farther the distance from a region to the optical axis of the detection optical system, the lower the MTF (Modulation Transfer Function) for the region, is solved by effectively utilizing the light quantity of a Gaussian light beam emitted by an ordinary low-cost light source, making it possible to detect also a defect caused by typically a very small extraneous material with a size in a range of about 0.1 $\mu$m s to about 0.5 $\mu$m or even a defect caused by typically a very small extraneous material with a size smaller than 0.1 $\mu$m with a high degree of sensitivity and at a high speed.

In addition, according to configuration described above, an optical image based on a DUV (Distant Ultra Violet) laser beam such as an excima laser obtained from a substrate serving as an object of inspection can be received by a TDI image sensor, making it possible to detect also a defect caused by typically a very small extraneous material with a size in a range of about 0.1 $\mu$m to about 0.5 $\mu$m or even a defect caused by typically a very small extraneous material with a size smaller than 0.1 $\mu$m.

Furthermore, according to a configuration described above, a problem of an insufficient illumination intensity on the periphery of an area of detection on a substrate serving as an object of inspection caused by the fact that, the farther the distance from a region to the optical axis of the detection optical system, the lower the MTF for the region, is solved by effectively utilizing the light quantity of a beam emitted by a lamp serving as a light source, making it possible to detect also a defect caused by typically a very small extraneous material with a size of about 0.1 $\mu$m or smaller in the area of detection with a high degree of sensitivity and at a high speed. It should be noted that the detection is moved from one area to another over the substrate serving as an object of inspection.

BRIEF DESCRIPTION OF THE DRAWINGS

FIG. 2(*b*) is a diagram showing the same in concrete terms as seen from a position on the x axis;

DETAILED DESCRIPTION OF THE PREFERRED EMBODIMENT

Some preferred embodiments implementing a defect inspecting apparatus and method provided by the present invention, are explained by referring to diagrams as follows.

By the way, with semiconductor devices miniaturized more and more, a further increase in yield is also required. To put it in detail, a circuit pattern created on a semiconductor substrate such as a semiconductor wafer for making such semiconductor devices is subjected to super miniaturization with a design rule of 0.3 to 0.2 μm or even smaller. For this reason, a foreign particle existing on the semiconductor substrate causes a semiconductor device created on the substrate to operate abnormally even if the foreign particle is an infinitesimal molecule with a size of about 0.1 μm or smaller or a particle with a size close to that at an atomic level.

In such a state of the art to fabricate a semiconductor device, the defect inspecting apparatus provided by the present invention for detecting a defect such as a foreign particle is required to have a capability of inspecting a defect such as an infinitesimal foreign particle existing on a semiconductor substrate such as a semiconductor wafer, on which a circuit pattern undergoing a super-miniaturization by a design rule of 0.3 to 0.2 μm or even smaller exists, with a high degree of sensitivity at a high speed.

Figure 1:
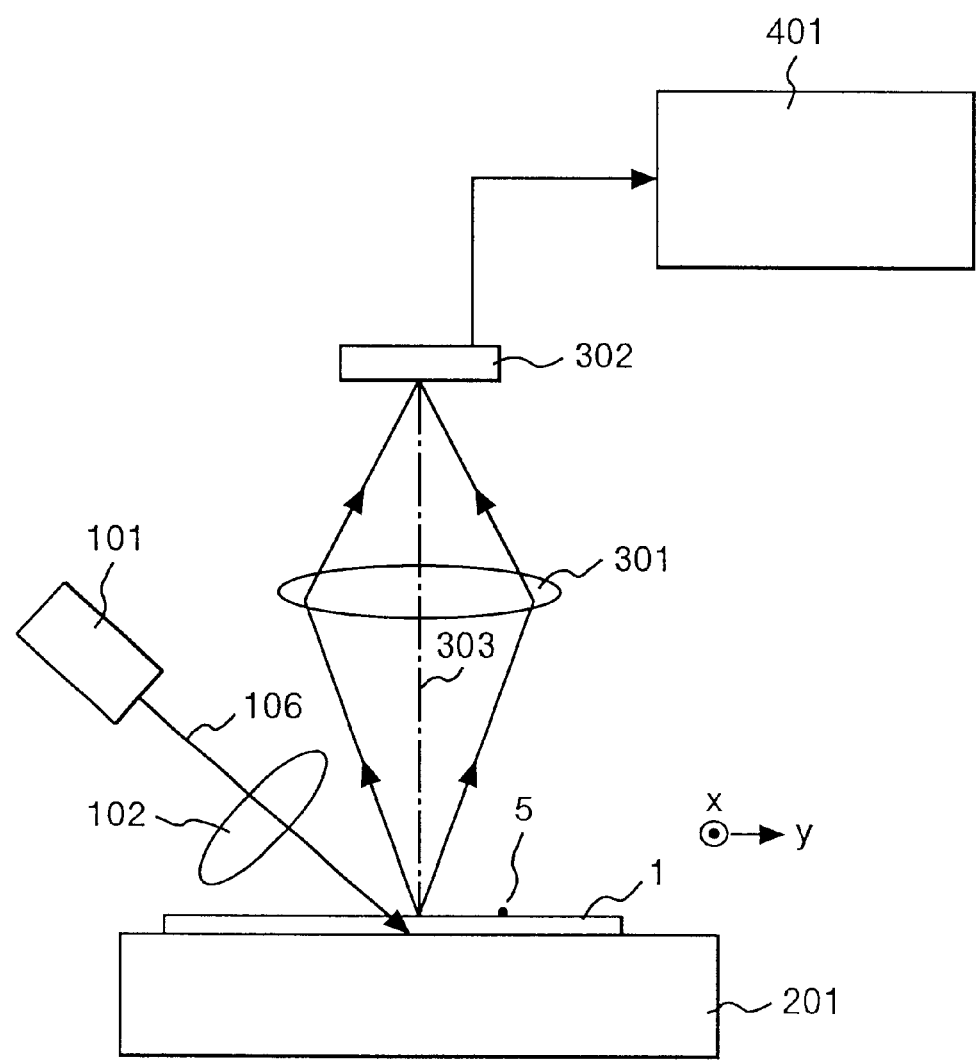
FIG. 1 is a diagram showing the configuration of a fourth embodiment implementing a defect inspecting apparatus provided by the present invention in a simple and plain manner.
Figure 2A:
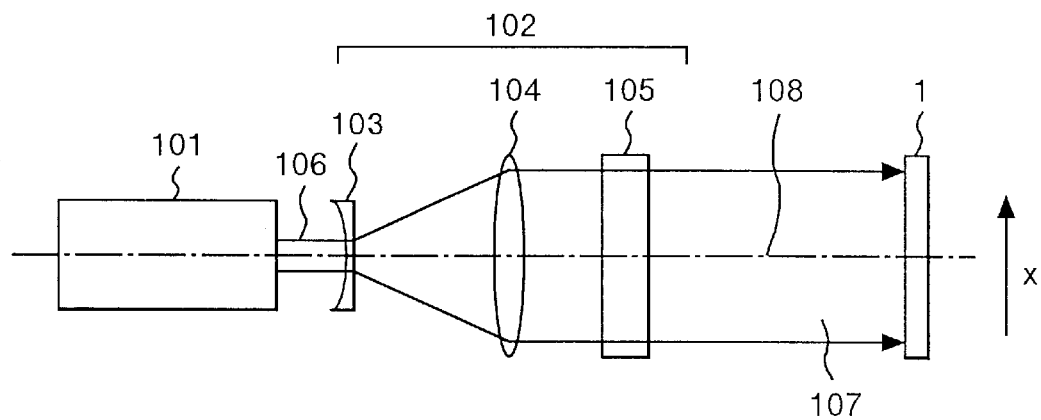
FIG. 2(*a*) is a diagram showing an embodiment implementing an illumination optical system employed in the fourth embodiment implementing a defect inspecting apparatus of FIG. 1 in concrete terms as seen from a position on the y axis.
Figure 2B:
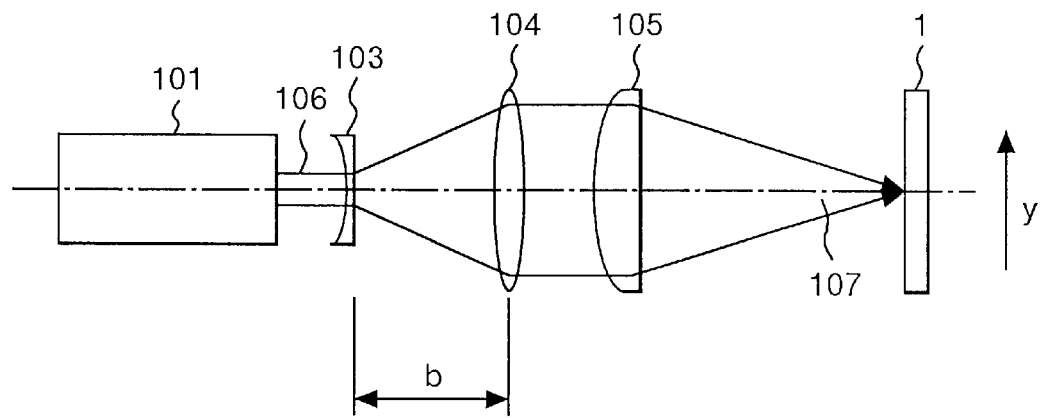

FIG. 1 is a diagram showing the first embodiment implementing a defect inspecting apparatus provided by the present invention for detecting a defect such as a foreign particle in a simple and plain manner. FIG. 2 is a diagram showing an embodiment implementing an illumination optical system employed in the defect inspecting apparatus.

Figure 3:
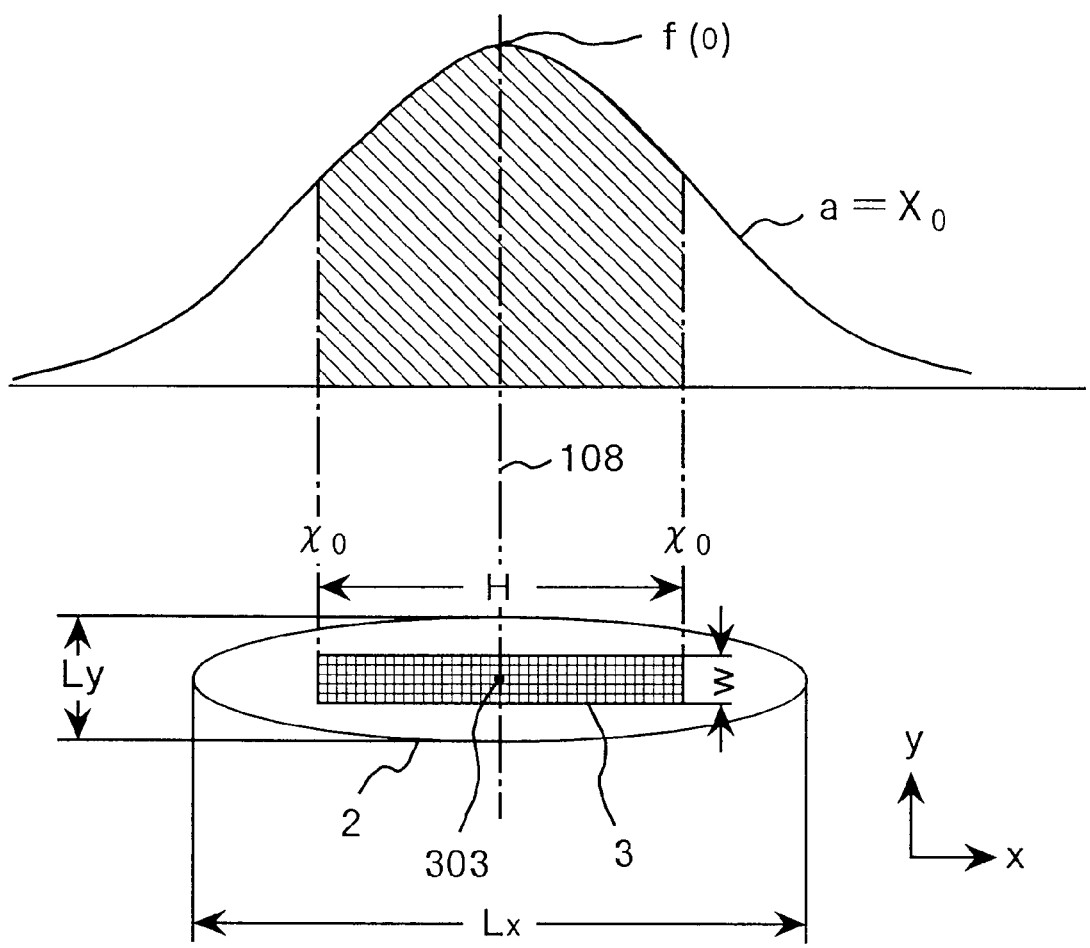
FIG. 3 is an explanatory diagram used for describing a basic concept of shaping a slit-shaped Gaussian beam by means of an illumination optical system to increase the illumination efficiency.

As shown in FIG. 1, the defect inspecting apparatus for detecting a defect such as a foreign particle comprises: stage 201 for mounting an inspection object 1 such as a semiconductor device or a semiconductor wafer on which a super-miniaturized circuit pattern with a defect thereof to be detected has been created; an illumination-light source 101 implemented by a laser-beam source such as a semiconductor laser, an argon laser, a YAG-SHG laser or an excima laser; an illumination optical system 102 for radiating a high-luminance light emitted by the illumination-light source (laser source) 101 to an illumination area 2 on the inspection object 1 from a slanting direction as a slit-shaped Gaussian beam 107 having a illumination distribution close to the Gaussian distribution as shown in FIG. 3; a detection optical system 301 comprising an image formation lens includes an objective lens which are used for forming an image from reflection lights, or diffraction lights or scattered lights obtained by a detection area 3; detector 302 each implemented typically by a TDI image sensor or a CCD image sensor having a photo-sensitive surface corresponding to the detection area 3; and an image-signal processing unit 401 for detecting a defect such as a foreign particle from an image signal output by the detector 302.

It should be noted that the defect inspecting apparatus also has an automatic focus control system for controlling formation of an image of the surface of the inspection object 1 on the photo-sensitive surface of the detector 302.

The detection optical system 301 may be formed of a spatial filter unit for shielding diffraction light coming from repetitive patterns having a small pitch formed on a substrate to be inspected, and Fourier transform lens as described in Japanese Patent Laid-open Nos. Hei 6-258239 and Hei 6-324003.

The actual configuration of the illumination-light optical source 101 and the illumination optical system 102 is shown in FIG. 2. In the figure, reference numeral 103 denotes a concave or convex lens for enlarging the diameter of a laser beam 106 emitted by the illumination-light source 101. Reference numeral 104 denotes a collimate lens for converting a laser beam output by the concave or convex lens 103 with an expanding diameter into substantially parallel beams. Reference numeral 105 denotes a cylindrical lens with a conical surface for converging the substantially parallel beams obtained as a result of the conversion in the collimate lens 104 in the direction of the y axis and for radiating the converged beams to an illumination area 2 on the inspection object 1 as a slit-shaped Gaussian beam 107 having an illumination distribution close to the Gaussian distribution as shown in FIG. 3. The cylindrical lens 105 serves as an optical system having a converging function in the direction of the y axis.

It should be noted that the concave or convex lens 103 and the collimate lens 104 constitute a beam expander for enlarging the diameter of the laser beam 106. Thus, the illumination optical system 102 can be regarded as a system comprising the beam expander, the cylindrical lens 105 and a mirror as described in Japanese Patent Laid-open Nos. Hei 6-258239 and Hei 6-324003. The beam expander typically comprises a collimate lens, a concave lens and a receiver lens. As described above, the cylindrical lens 105 is used for converging the substantially parallel beams obtained as a result of the conversion in the beam expander in the direction of the y axis and for radiating the converged beams to an illumination area 2 on the inspection object 1 as a slit-shaped Gaussian beam 107 having an illumination distribution close to the Gaussian distribution as shown in FIG. 3. The mirror reflects the slit-shaped Gaussian beam 107 output by the cylindrical lens 105 and radiates the beam 107 to the inspection object 1 in a slanting direction.

By the way, by changing the distance b between the concave or convex lens 103 and the collimate lens 104 or the distance between the concave lens and the receiver lens in the configuration described above, the x-direction width of the luminance beam having an illumination distribution substantially resembling the Gaussian distribution can be altered. That is to say, by adjusting the beam expander, the x-direction length Lx of the illumination area 2 (or the slit-shaped beam 107) having an illumination distribution substantially resembling the Gaussian distribution can be changed. In addition, by varying the distance between the conical lens 104 and the inspection object 1, the y-direction length Ly of the illumination area 2 (or the slit-shaped beam 107) having an illumination distribution substantially resembling the Gaussian distribution can also be changed.

Figure 4A:
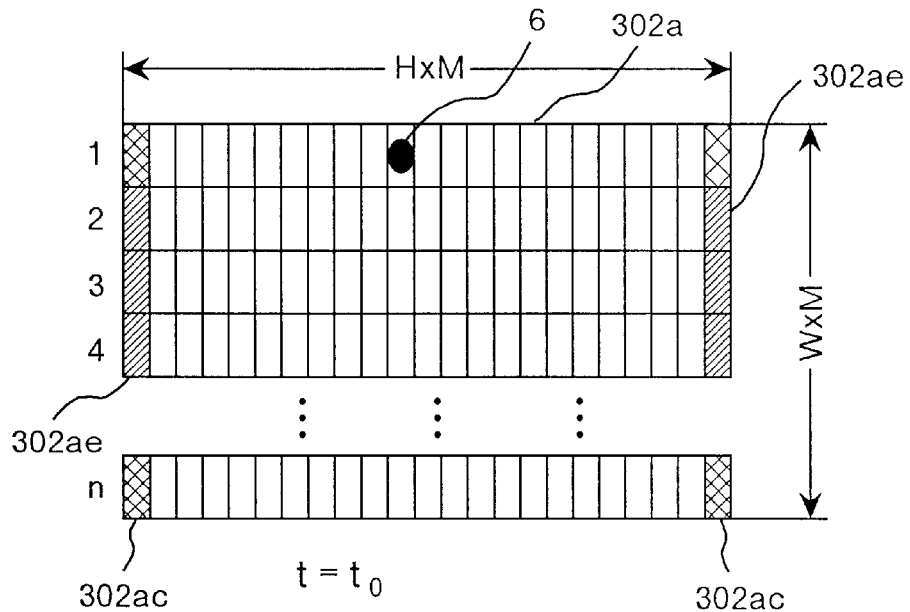
FIGS. 4(*a*) and 4(*b*) are explanatory diagrams used for describing an image-pickup method to receive a light representing an optical image in an area of detection on a substrate being inspected by using a TDI image sensor as a detector.
Figure 4B:
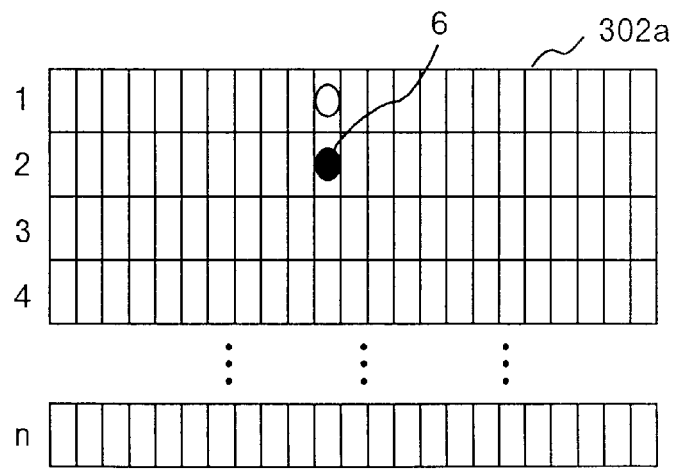

A detection area 3 shown in FIG. 3 is an area on the inspection object 1 to be inspected by using a TDI image sensor or a CCD image sensor. In the case of a TDI image sensor, for example, the dimensions of each pixel are typically 27 μm×27 μm. The TDI image sensor is typically a 64×4,096 CCD image-pickup sensor which comprises 64 rows in the TDI (Time Delay Integration) direction and 4,096 columns in the MUX direction, and operates in a TDI mode. That is to say, the TDI image sensors 302a has a configuration comprising n stages of line sensors as shown in FIG. 4 where n is typically 64. A line rate rt is the amount of information output by the sensor which is the line sensors in this case. At a line rate rt, accumulated charge is transferred through lines 1, 2 and so on, from one line to another. By synchronizing the movement speed of the y-axis stage 201 for moving the inspection object 1 in the direction of the y axis with the line rate rt, an image 6 based on a scattered light and a diffraction light generated by typically an infinitesimal foreign particle 5 is accumulated for a long time it takes to transfer the charge to the line n so that a defect such as an infinitesimal foreign particle can be detected with a high degree of sensitivity. In this image sensor, the image of a defect such as an infinitesimal foreign particle is detected as a sum of intensities of a scattered light and a diffraction light traveling from the line 1 to the line n. However, a scattered light or a diffraction light coming from the same point on the object of inspection and reaching the lines is timewise entirely incoherent.

As described above, a beam emitted by the illumination-light source 101 is converted by the illumination optical system (or the radiation optical system) 102 into a slit-shaped Gaussian beam 107 which is radiated to the surface of the inspected substrate 1 on the stage 201 typically in a slanting direction to form an illumination area 2 on the surface. While the inspected substrate 1 is being moved in the direction of the y axis by moving the stage 201 in the direction of the y axis, the detector 302a implemented typically by a TDI image sensor transfers electric charge accumulated in each pixel from one line to another at a line rate rt synchronized with the movement speed of the stage 201. In this way, while an optical image of the detection area 3 on the inspected substrate 1 formed by the detection optical system 301 is being picked up, each pixel (or each device) along the width H of the detection area 3 is scanned to generate a detection signal which is then supplied to the image-signal processing unit 401. By processing the detection signal in the image-signal processing unit 401, it is possible to detect a defect such as an infinitesimal foreign particle existing in the detection area 3 with a high degree of sensitivity and at a high speed.

By using the TDI image sensor 302a as described above, it is possible to compute a total of illumination values of a scattered light or a diffraction light generated by a defect such as an infinitesimal foreign particle where (quantity of light=illumination value×time) and, hence, to increase the sensitivity. In addition, once the slit-shaped beam 107 is radiated to the radiation area 2 and, a light generated by the detection area 3 is received by the TDI image sensor 302a while the inspected substrate 1 is being moved in the direction of the y axis in synchronization with the line rate rt of the TDI image sensors so that it is possible to detect a defect such as an infinitesimal foreign particle existing in the detection area 3 with a large width H at a high speed.

The following description further describes the fourth embodiment of the present invention for detecting a defect such as an infinitesimal foreign particle with a size of about 0.1 μm or smaller with a high degree of sensitivity and at a high speed. That is to say, when it is desired to detect a defect such as an infinitesimal foreign particle with a size of about 0.1 μm or smaller with a high degree of sensitivity, it is necessary to increase the intensity of a scattered light or a diffraction light generated by a defect such as an infinitesimal foreign particle and received by pixels of a TDI image sensor 302a and also to reduce the dimensions of each pixel on the inspected substrate 1 to about 1 μm×1 μm or smaller.

It is possible to realize an implementation wherein the dimensions of each pixel on the inspected substrate 1 are reduced to about 1 μm×1 μm or smaller as described above by setting the image formation magnification M of the detection optical system 301 including an objective lens at a value of about 27 times or larger for dimensions of each pixel on the TDI image sensors of typically 27 μm×27 μm. It should be noted that, if 26×4,096 CCD pickup sensors are used as the TDI image sensor 302a, the detection area 3 will have a width W not exceeding a value of about 26 μm and a height H not exceeding a value of about 4,096 μm.

In addition, the detection optical system 301 for forming an image in photo-sensitive areas on the TDI image sensor 302a from an optical image formed by a scattered light or a diffraction light generated by the surface of the inspected substrate 1 includes an objective lens having a characteristic which, due to lens aberration, shows the fact that, the farther a position from the center of the lens (or the optical axis 303), that is, the closer a position to a periphery, the smaller the MTF (Modulation Transfer Function) at the position. The MTF represents changes in contrast of an image of a sinusoidal wave pattern as a function of spatial frequency. For this reason, it is necessary to increase the intensity of a scattered light or a diffraction light generated by pixel 302ae on the edge (or the periphery) with a smallest MTF located farthest from the optical axis 303 on the photo-sensitive surface of the TDI image sensor 302a shown in FIG. 4(a), or generated by a defect such as an infinitesimal foreign particle located on the edge (or the periphery) with a smallest MTF farthest from the optical axis 303 in the detection area 3 shown in FIG. 3.

By the way, the illumination of the slit-shaped Gaussian beam 107 radiated to the radiation area 2 on the surface of the inspected substrate 1 by the illumination-light source 101 and the illumination optical system 102 exhibits the ordinary Gaussian distribution as shown in FIG. 3, wasting illumination outside the detection area 3. On the other hand, it is necessary to illuminate the illumination area 2 which is made larger than the detection area 3.

In order to solve this problem, in this present invention, the quantity of a light emitted by the illumination-light source 101 is utilized effectively and the illumination on the edge (or the periphery) with a smallest MTF farthest from the optical axis 303 in the detection area 3 is increased most without increasing the illumination of the light in order to detect a defect such as an infinitesimal foreign particle with a size of about 0.1 μm or smaller with a high degree of sensitivity. That is to say, by employing a low-cost illumination-light source 101 for emitting a light with a minimum required illumination, the illumination on the edge (or the periphery) with a smallest MTF farthest from the optical axis 303 in the detection area 3 can be increased most by the illumination optical system 102 to implement illumination with a high degree of efficiency. Examples of such a low-cost illumination-light source 101 are a laser-beam source such as a semiconductor laser, an argon laser, a YAG-SHG laser or an exima laser and a filament light source such as a canon lamp, an electric-discharge tube such as mercury lamp and a halogen lamp.

To put it concretely, in the present invention, when the illumination-light source 101 and the illumination optical system 102 radiates a slit-shaped beam 107 having an illumination of the Gaussian distribution to illuminate the illumination area 2 on the inspected substrate 1, the illumination optical system 102 is adjusted (or controlled) to set such a width of the illumination that the illumination on the periphery of the detection area 3 is maximized. The Gaussian distribution of the illumination of the slit-shaped beam 107 shown in FIG. 3 can be expressed by Eq. (1) given below. The illumination on the periphery of the detection area 3 is maximized when the expression on the right-hand side of Eq. (2) is equal to 0.

$$f(x_0) = \frac{1}{\sqrt{2\pi}\,\sigma}\exp\left(-\frac{1}{2\sigma^2}x_0^2\right) \quad (1)$$

$$\frac{\partial f(x_0)}{\partial \sigma} = \frac{1}{\sqrt{2\pi}}\left(1-\frac{x_0}{\sigma}\right)\left(1+\frac{x_0}{\sigma}\right)\exp\left(-\frac{1}{2\sigma^2}x_0^2\right) \quad (2)$$

The maximum illumination f(0) on the outermost circumference (edge) of the detection area 3 in the direction of the x axis corresponding to the photo-sensitive surfaces of the TDI image sensor 302a is about 60.7% of the luminance f(0) at the center of the detection area 3. This is because equating the expression on the right-hand side of Eq. (2)σ to 0 yields x0=σ (for σ=1, x0=1) and substituting σ for x0 in Eq. (1) results in the maximum value f(x0)=0.607f(0). It should be noted that, for x0=0.8σ to 1.2σ in Eq. (1), f(x0)=0.49f(0) to 0.73f(0). In this case, for σ=1, x0=0.8 to 1.2 (for the Gaussian beam 107, a reshaping error in the range ±20% caused by the illumination optical system 102 is allowable). For σ=0.8x0 to 1.2x0 in Eq. (1) which means that, for x0=1, σ=0.8 to 1.2 (for the Gaussian beam 107, a reshaping error in the range ±20% caused by the illumination optical system 102 is allowable), f(x0)=0.46f(0) to 0.71f(0). Thus, if a reshaping error of the Gaussian beam 107 in the range ±20% caused by the illumination optical system 102 is allowable for x0=σ (for σ=1, x0=1), the ratio of the illumination f(x0) on the outermost circumference (the periphery) of the detection area 3 to the illumination f(0) at the center (the optical axis 303) of the detection area 3 is in the range 0.46 to 0.73, or f(x0)=0.46f(0) to 0.73f (0). It should be noted that, if a reshaping error of the Gaussian beam 107 in the range ±10% caused by the illumination optical system 102 is allowable for x0=σ (for σ=1, x0=1), the ratio of the illumination f(x0) on the outermost circumference (the periphery) of the detection area 3 to the illumination f(0) at the center (the optical axis 303) of the detection area 3 is in the range 0.54 to 0.67, or f(x0)=0.54f(0) to 0.67f(0).

In either case, by a Gaussian beam 107 by means of the illumination optical system 102 so that the ratio of the illumination f(x0) on the outermost circumference (the periphery) of the detection area 3 to the illumination f(0) at the center (the optical axis 303) of the detection area 3 is set at a value in the range 0.46 to 0.73, the beam emitted by the illumination-light source 101 can be utilized effectively to increase the illumination on the periphery of the detection area 3 to a value close to a maximum.

Figure 5:
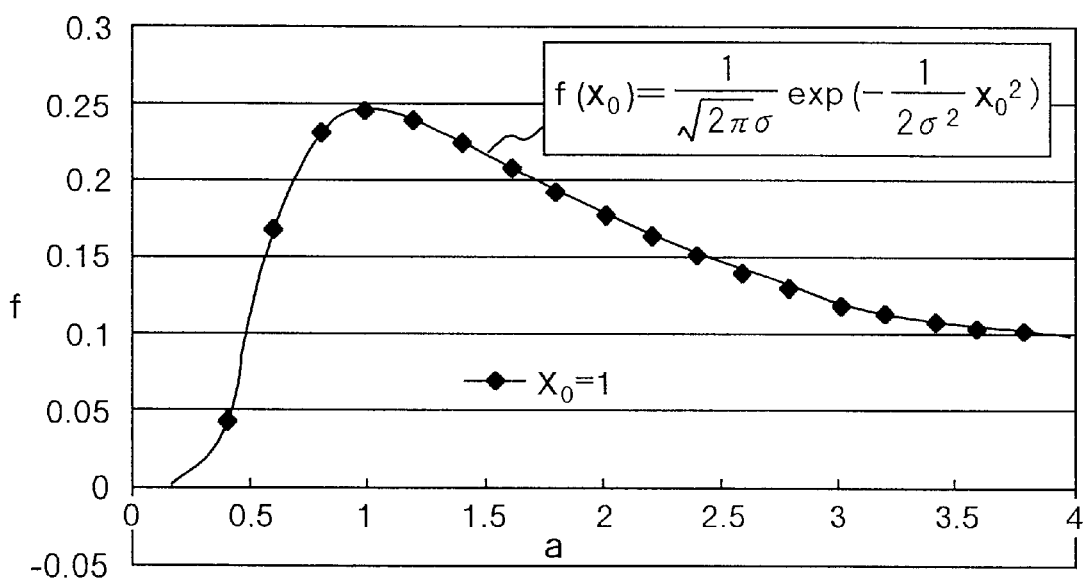
FIG. 5 is a diagram showing variations in illumination $f(x_0)$ at a periphery ($x_0$=1) of a detection area with changes in standard deviation $\sigma$ (corresponding to the width of illumination) of a Gaussian Beam.

FIG. 5 is a diagram showing a graph representing a relation between the width of illumination in the direction of the x axis or the standard deviation σ and the illumination (or the quantity of light per unit area) f(x0=1) on a circumference (x0=1) in the direction of the x axis in the detection area 3 for a fixed quantity of a light or a fixed total illumination of a light emitted by the illumination-light source 101.

Figure 6:
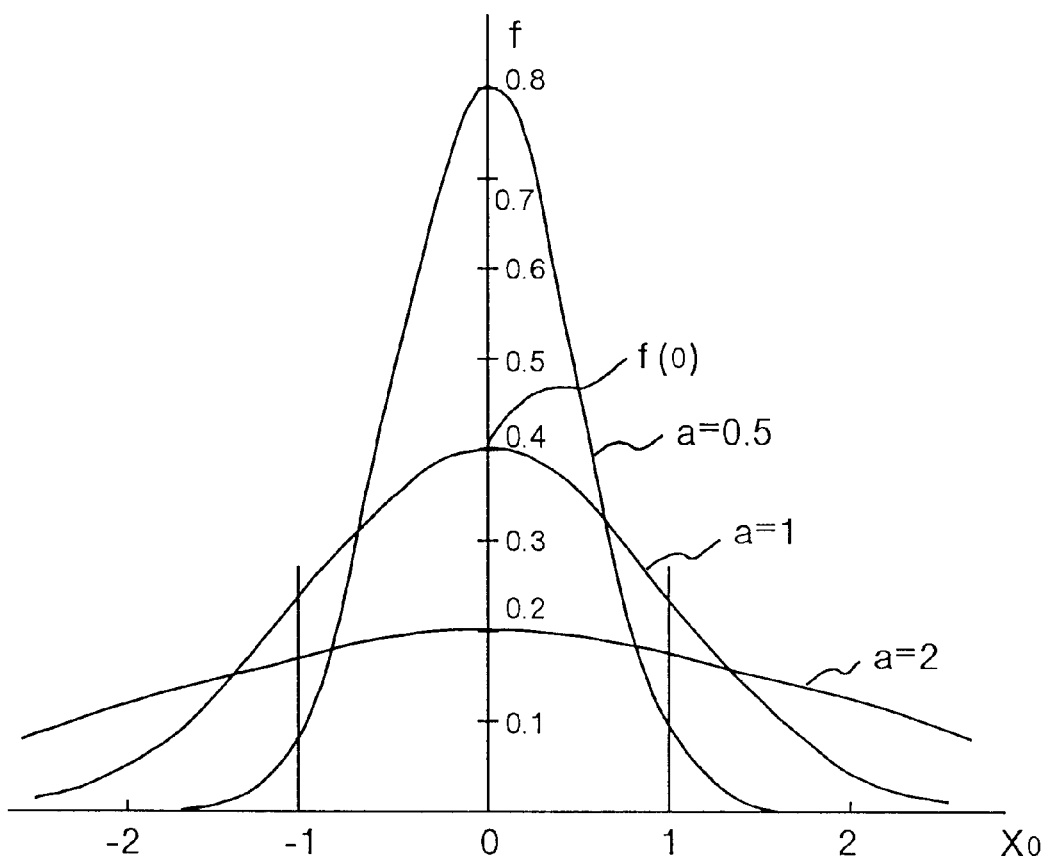
FIG. 6 is a diagram showing variations in illumination $f(x_0)$ with changes in distance $x_0$ from the optical axis of a detection area for a radiated Gaussian beam at standard deviations $\sigma$ of 0.5, 1 and 2.

FIG. 6 is a diagram showing graphs each representing a relation between the coordinate x0 in the direction of the x axis in the detection area 3 and the illumination (or the quantity of light per unit area) f(x0) for a fixed quantity of a light or a fixed total illumination of a light emitted by the illumination-light source 101 with the width of illumination or the standard deviation σ taken as a parameter. The figure shows graphs for parameter values of 0.5, 1 and 2.

As is obvious also from FIGS. 5 and 6, in order to set the illumination on a circumference (x0=1) in the direction of the x axis in the detection area 3 at a value close to a maximum, the beam is radiated with the width σ of the illumination in the direction of the x axis based on the Gaussian distribution generated by the illumination optical system 102 set at a value of about 1 (that is, the standard deviation σ=x0). Let x0 denote the distance from the center of the detection area 3 or the optical axis to the circumference in the direction of the x axis as shown in FIG. 3. In this case, if the illumination optical system 102 reshapes a light emitted by the illumination-light source 101 into a slit-shaped beam 107 having an illumination of the Gaussian distribution for a standard distribution σ substantially equal to x0 (which is the distance from the center of the detection area 3 or the optical axis to the circumference in the direction of the x axis as described above) and radiates the beam 107 to the illumination area 2 on the inspected substrate 1, the illumination on a circumference (x0=1) can be maximized. It should be noted that the illumination area 2 is an area with f equal to at least 0.2×f(0) where the symbol f denotes the illumination on the circumference indicated by Lx and Ly.

It should be noted that, in actuality, TDI image sensors or 2-dimensional linear image sensors are used as the detector 302. In this case, a pixel with a smallest MTF separated farthest from the optical axis 303 is located at a corner of the detection area 3. In the case of a TDI image sensor, pixels with a smallest MTF separated farthest from the optical axis 303 are pixel 302ac located at the corners as shown in FIG. 4. Thus, it is desirable to set x0 at the square root of $((H/2)^2+(W/2)^2)$ where the symbols H and W respectively denote the width (the length) in the direction of the x axis and the width in the direction of the y axis of the detection area 3 on the inspected substrate 1. If W can be ignored, x0=(H/2). The width in the direction of the x axis and the width in the direction of the y axis of a photo-sensitive area (an image-pickup area) on the TDI image sensor or the 2-dimensional linear image sensor are thus (H×M) and (W×M) respectively. It should be noted that the symbol M denotes the magnification of the image-formation optical system 201.

As described above, by setting the coordinate x0 of the circumference in the direction of the x axis in the detection area 3 (or in the case of a TDI image sensor or a 2-dimensional linear image sensor, the coordinate x0 of pixels separated farthest from the optical axis 303) at the square root of $((H/2)^2+(W/2)^2)$ or (H/2) and by having the illumination optical system 102 reshape a light emitted by the illumination-light source 101 into a slit-shaped beam 107 having an illumination of the Gaussian distribution for a standard distribution σ substantially equal to x0 and radiate the beam 107 to the illumination area 2 on the inspected substrate 1 where the illumination area 2 is an area with f equal to at least 0.2×f(0) where the symbol f denotes the illumination on the circumference indicated by Lx and Ly, high-efficiency illumination can be implemented by using a low-cost ordinary illumination-light source 101 without the need to employ a special illumination-light source with a high power output. Examples of such a low-cost illumination-light source 101 are a laser-beam source such as a semiconductor laser, an argon laser, a YAG-SHG laser or an exima laser and a filament light source such as a xenon lamp, an electric-discharge tube such as mercury lamp and a halogen lamp. As a result, the detection optical system 201 is capable of increasing the intensity of a scattered light or a diffraction light generated by a defect such as an infinitesimal foreign particle receiving a light radiated to pixels on the peripheries of the detector 302 with a lowest MTF. Thus, a defect such as an infinitesimal foreign particle with a size in the range around 0.1 to 0.5$\mu$m or even an infinitesimal foreign particle with a size smaller than about 0.1 $\mu$m can be detected with a high degree of sensitivity and at a high speed (or at a high throughput). It should be noted that, even though the illumination in an area in the direction of the x axis varies in dependence on the coordinate x0 as indicated by $f(x0)=0.46 \times f(0)$ to $0.73 \times f(0)$, the inspection object 1 is moved in the direction of the y axis so that the image-signal processing unit 401 compares an image signal with another image signal obtained from the same pixel array in the direction of the x axis in the detection area 3 detected by the detector 302 which are each implemented typically by a TDI image sensor. Thus, there is substantially no effect of the difference in illumination between the center and the periphery. Then, the image-signal processing unit 401 extracts a difference in image signal between chips or cells which are repeated in the same circuit pattern on the basis of image signals detected by the detector 302 implemented typically by a TDI image sensor while the inspection object 1 is being moved in the direction of the y axis. By comparing the extracted difference in image signal using a desired criterion, a defect such as a foreign particle can be detected during the inspection.

In this case, the fact that the illumination (or the quantity of light) on the periphery of the detection area 3 is increased to a value close to a maximum is important. In this embodiment, the illumination on the periphery of the detection area 3 is increased to a value close to a maximum by changing the width of the illumination by means of the illumination optical system 102. As an alternative, the illumination on the periphery of the detection area 3 is increased to a value close to a maximum by changing the shape of a secondary light source of the illumination by means of the illumination optical system 102. As another alternative, the illumination on the periphery of the detection area 3 is increased to a value close to a maximum by varying the size at the location of a Fourier transformation for forming the secondary light source.

The embodiment described above is used to exemplify inspection of a substrate 1 serving as an object of inspection for a defect caused by typically an extraneous material stuck on the surface of the substrate. Normally, inspection of a circuit pattern for a defect comprises the steps of using a $\lambda/4$ plate to convert a P or S polarized light transmitted through or reflected by a polarized-light splitter placed above a first objective lens of the detection optical system 301 into a circular polarized light, radiating a split-shaped beam 107 of the circular polarized light to an area of illumination 2 on the inspected substrate 1 by way of a second objective lens in the downward direction, letting circular lights reflected, diffracted or scattered by an area of detection 3 on the inspected substrate 1 pass through a third objective lens, using a $\lambda/4$ plate to convert the lights transmitted through the third objective lens into a P or S polarized light, letting the P or S polarized light be reflected by or transmitted through the polarized-light beam splitter, and using a pair of Fourier transformation lenses to form an image on the detector 302 implemented by typically a TDI image sensor.

Then, by using a picture signal detected by the detector 302 implemented by typically a TDI image sensor as a base with the inspected substrate 1 moved in the y-axis direction, the signal processing system 401 is capable of detecting a defect existing in a circuit pattern by extracting a difference in picture signal between cells or between chips which are a repetition of the same circuit pattern and by comparing the extracted difference in picture signal with a desired criterion. Also in the inspection of circuit patterns for a defect, the radiation optical system 102 shapes the beam emitted by the light source 101 into a split-shaped optical beam 107 exhibiting a Gaussian distribution of illumination intensities with a standard deviation $\sigma$ about equal to x0 which is the distance from the center of the area of detection 3 to a periphery in the x-axis direction. In the case of a TDI image sensor or a 2-dimensional linear image sensor, the periphery is a pixel most separated away from the optical axis 303. The distance x0 is the square root of $\{(H/2)^2+(W/2)^2\}$ or $H/2$ where the symbols H and W represent the height (the dimension in the x-axis direction) and the weight (the dimension in the y-axis direction) of the area of detection 3 respectively. The radiation optical system 102 then radiates the shaped optical beam 107 to the area of illumination 2 on the substrate 1 serving as an object of inspection in the downward direction. Thus, by using an ordinary low-cost illumination light source 101, it is possible to implement illumination with a high degree of efficiency without the need to resort to a special illumination light source with a large power. Examples of the ordinary low-cost illumination light source 101 are laser sources such as a semiconductor laser, an Argon laser, a YAG-SHG laser and an exima laser, discharges tubes such as a canon lamp and a mercury lamp and filament light sources such as a halogen lamp. As a result, the detection optical system 301 is capable of increasing the intensity of a diffracted or scattered light originated from a defect in a circuit pattern and received by a pixel on the periphery of the detector 302 with a smallest MTF, making it possible to detect also a defect caused by typically a very small extraneous material with a size in a range of about 0.1 $\mu$m to about 0.5$\mu$m in the area of detection or even a defect caused by typically a very small extraneous material with a size smaller than 0.1 $\mu$m in the area of detection with a high degree of sensitivity and at a high speed (that is, at a high throughput).

The following description explains a second embodiment implementing a defect inspecting apparatus provided by the present invention.

Figure 7:
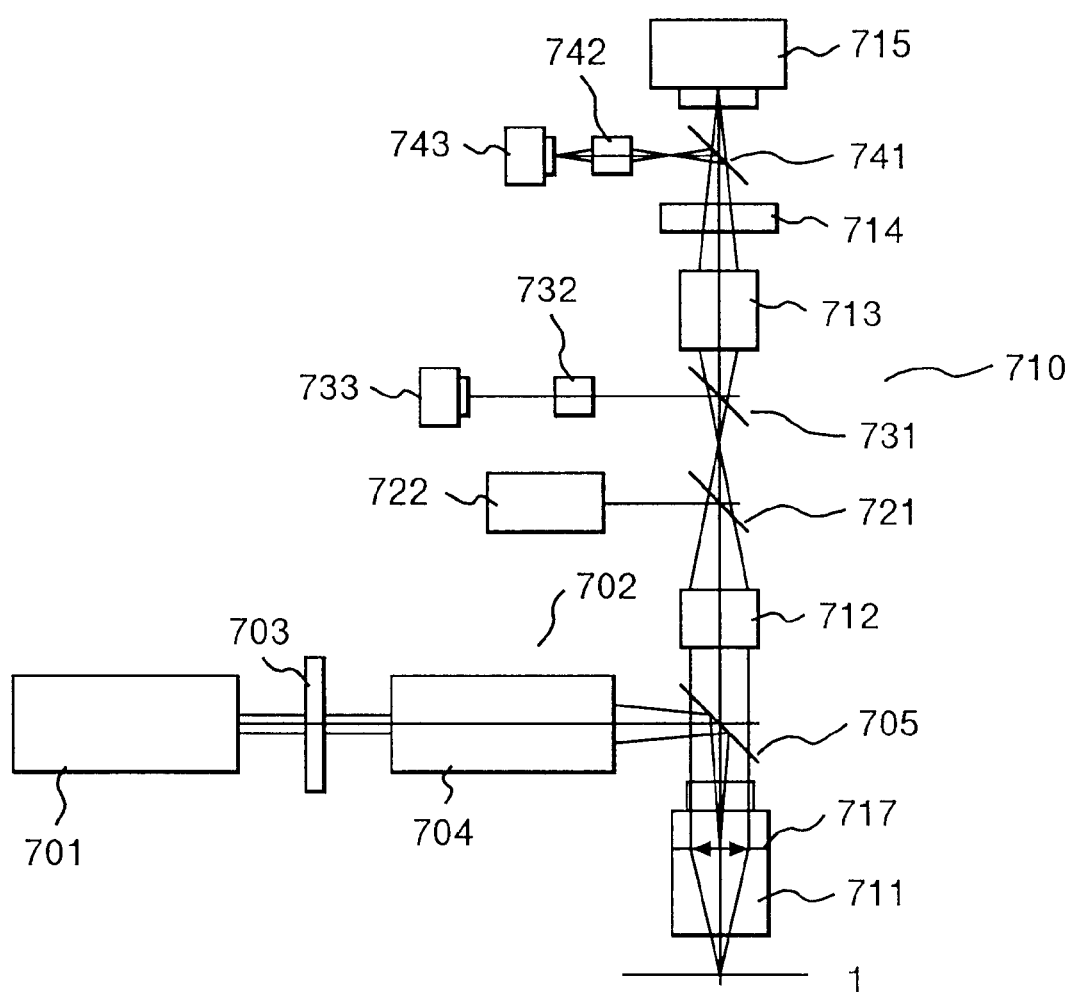
FIG. 7 is a diagram showing the configuration of the second embodiment implementing a defect inspecting apparatus provided by the present invention in a simple and plain manner.

FIG. 7 is a diagram showing the configuration of the second embodiment implementing a defect inspecting apparatus provided by the present invention in a simple and plain manner. In the second embodiment, the radiation optical system has a downward-illumination configuration. As an illumination light source 701, the second embodiment employs a DUV (Distant Ultra Violet) laser such as an excima laser with KrF=248 nm or an excima laser with ArF =193 nm. Having a small wavelength, the DUV laser exhibits a high resolution, making it possible to obtain an optical image based on scattered or diffracted lights originating from a defect caused by typically a very small extraneous material with a size of about 0.1 $\mu$m or smaller. In the second embodiment, the radiation optical system 702 comprises the illumination light source 701 implemented by typically a DUV laser, a polarization control optical system 703 for setting polarization of an illumination light, an eye scanning radiation optical system 704 for scanning an eye 717 of an objective lens 711 with a laser light and a first half mirror 705. The basic configuration of the detection optical system 710 includes an objective lens 711, an image forming lens 712, an enlargement optical system 713, a polarized-light detecting optical system 714 for setting polarization of a detected light in front of an image sensor 715 and the image sensor 715 with a DUV quantization efficiency of at least about 10%. In addition, on the path of a detected light, there are provided a second half mirror 721 and an automatic focusing system 722 for adjusting the surface of a sample 1 to the focus of the objective lens 711. Furthermore, a third half mirror 731 is provided so that the eye position of the objective lens 711 can be observed by a first lens 732 and an eye observing optical system 733. Moreover, a fourth half mirror 741 is provided so that a pattern on the sample 1 can be observed and aligned by a second lens 742 and an alignment optical system 743.

In the configuration described above, a DUV laser beam emitted by the illumination light source 701 is converted by the polarization control optical system 703 into a straight-line polarized light which is radiated by the eye scanning radiation optical system 704 to the eye 717 of the objective lens 711 in order to scan the eye 717 two-dimensionally. A beam reflected by the sample 1 passes through the eye 717 of the objective lens 711 and the first half mirror 705, being formed into an image on the image sensor 715 by the image forming lens 712 for forming an image of the sample 1 and the enlargement optical system 713. It should be noted that the polarized-light detecting optical light 714 optically blocks a straight-line polarized-light component radiated to the sample 1 so that the image sensor 715 receives an optical image formed from a scattered-light or diffracted-light component originating from the surface of the sample 1.

Figure 8A:
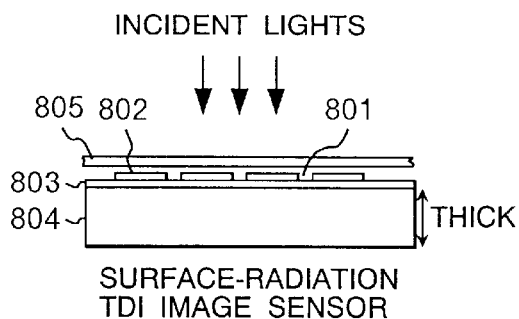
FIGS. 8(*a*) and 8(*b*) are explanatory diagrams used for describing an embodiment implementing a TDI image sensor capable of receiving a DUV light.

In addition, since a DUV (deep ultraviolet) laser source is employed as the illumination-light source 701, it is necessary to use image sensor 715 that is sensitive to a DUV laser. If surface-radiation TDI image sensor shown in FIG. 8(a) are employed as the image sensor 715, however, an incident light passes through a cover glass 805, gates 801 between metallic films 802 and an oxide film ($SiO_2$ film) 803 before hitting CCDs created on an Si substrate 804. Thus, since an incident light having a small wavelength is attenuated, the sensor becomes substantially insensitive to a light with a wavelength of 400 nm or smaller. As a result, the DUV light may not be detected. In order to make the surface-radiation TDI image sensor sensitive to a DUV light, there is provided a technique whereby the thickness of the oxide film 803 beneath the gates 801 is reduced so that the amount of attenuation of a light with a small wavelength is decreased. As another technique, the cover glass 805 is coated with an organic thin film. With such an organic thin film, a visible light is emitted in accordance with an incident DUV light. In this way, the DUV light is detected as a visible light by a sensor that is sensitive only to the visible light.

Figure 8B:
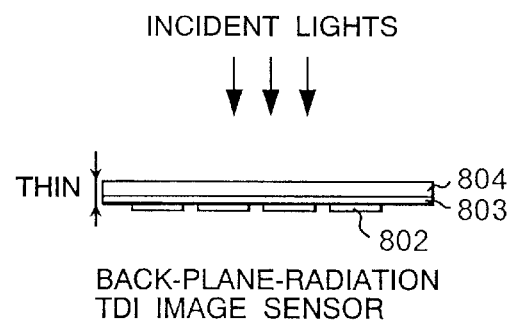

On the other hand, the thickness of the Si substrate 804 is reduced as shown in FIG. 8(b) to provide back-surface-radiation TDI image sensors which each receive an incident light hitting the thin Si substrate 804 on the rear side as the image sensor 715. Since an incident light hits the surface on the rear side including no gate structure, the DVD quantization efficiency is increased by about 10% or more to give a high quantization efficiency and a large dynamic range. As a result, the sensor becomes sensitive to a light having a wavelength of 400 nm or smaller. In addition, by having the image sensor 715 go TDI (Time Delay Integration) as described above, the sensitivity can be improved.

Figure 9:
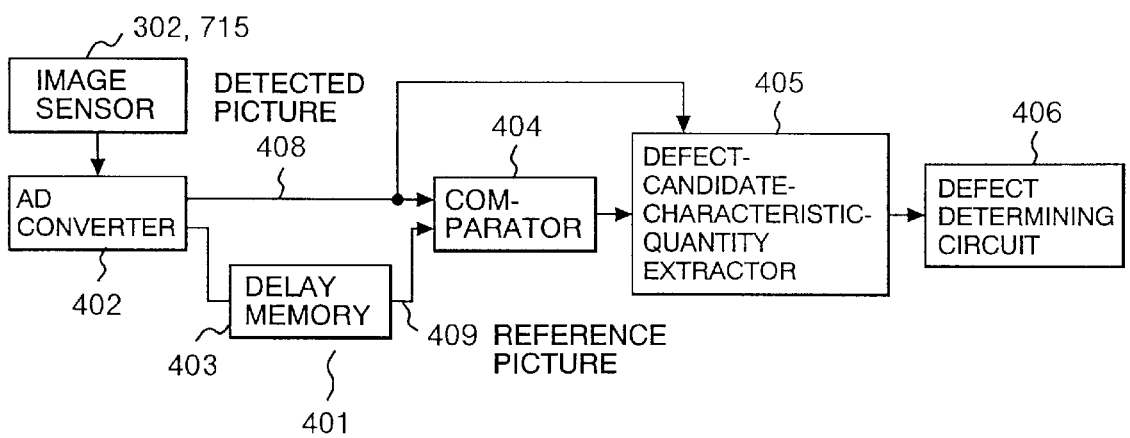
FIG. 9 is a diagram showing the configuration of an embodiment implementing a signal processing system capable of inspecting an object by detection of a signal generated by a defect caused by typically a very small extraneous material with a size of about 0.1 μm or smaller by discrimination of a false-information signal.

Next, the signal processing system 401 is explained concretely by referring to FIG. 9. As shown in the figure, the signal processing system 401 comprises an AD conversion circuit 402 for converting an analog picture signal generated by an image sensor 302 or 715 implemented by typically a TDI image sensor into a digital picture signal wherein the analog picture signal is represented by a concentration value stored for each array of pixels obtained in synchronization with the movement of the substrate 1 serving as an object of inspection in the y-axis direction; a delay memory 403 for delaying the digital picture signal output by the AD conversion circuit 402 by a delay time corresponding to typically 1 or a plurality of pitches of repetitive circuit patterns created on the substrate 1 serving as an object of inspection in the y-axis direction; a comparison circuit 404 for comparing a digital detected picture signal 408 output by the AD conversion circuit 402 with a digital reference picture signal 409 read out from the delay memory 403 to produce typically a differential picture signal, and for converting the differential picture signal into a binary picture signal representing a defect candidate for typically a defect caused by an extraneous material or a defect of a circuit pattern by comparing the differential picture signal with a predetermined threshold value; a defect-candidate-characteristic-quantity extracting circuit 405 for extracting characteristic quantities of the defect candidate for typically a defect caused by an extraneous material or a defect of a circuit pattern from the binary picture signal output by the comparison circuit 404 to represent the candidate; and a defect determining circuit 406 for determining that the defect candidate is a defect if the characteristic quantities of the defect candidate output by the defect-candidate-characteristic-quantity extracting circuit 405 exceed predetermined criteria.

Examples of characteristic quantities of a defect candidate are the area, the coordinate position, the maximum length and the moment of the defect candidate. By the maximum length, projection lengths (or maximum lengths) in the x-axis and y-axis directions are meant. It should be noted that, in addition to the characteristic quantities described above, a concentration value based on the digital detected picture signal output by the AD conversion circuit 402 can also be used as a further additional quantity for justifying a defect candidate. With such a concentration value added, 3-dimensional characteristic quantities are obtained. Particularly, in order to detect a defect caused by typically a very small extraneous material with a size of about 0.1 $\mu$m or smaller, it is necessary to avoid incorrect detection which can be prevented by eliminating a noise component generated by infinitesimal unevenness of the surface of the substrate 1 serving as an object of inspection. In the configuration described above, a differential picture signal exceeding a predetermined threshold value is extracted as a tentative candidate for a defect caused by typically an extraneous material. It is necessary to further confirm a real defect caused by a very small extraneous material by formation of a judgment as to whether the candidate is a real defect caused by a very small extraneous material or a state caused by infinitesimal unevenness of the surface. The judgment is based on the characteristic quantities of the defect candidate extracted by the defect-candidate-characteristic-quantity extracting circuit 405.

To put it in detail, on the substrate 1 serving as an object of inspection, repetitive circuit patterns are formed. The comparison circuit 404 compares a digital detected picture signal 408 output by the AD conversion circuit 402 with a digital reference picture signal 409 read out from the delay memory 403. The digital detected picture signal 408 is originated from a currently scanned circuit pattern whereas the digital reference picture signal 409 is originated from another circuit pattern adjacent to the currently scanned circuit pattern or separated away from the currently scanned circuit pattern by 1 pitch. A result of comparison is typically a differential picture signal representing a difference in pixel value between the digital detected picture signal 408 the digital reference picture signal 409. The differential picture signal is converted into a binary picture signal representing defect candidate points by comparing the differential picture signal with a threshold value set for extraction of the defect candidate points. An example of the set threshold value is a predetermined threshold value and a threshold value found from an attribute such as the brightness of the picture being inspected. At any rate, the threshold value is applied to the whole differential picture signal to convert the signal into binary data. Another example of the set threshold value is a threshold value computed for each coordinate position or each degree of brightness of the differential picture signal. In this case, different threshold values are used for conversion of the differential picture signal into binary data at different points of the differential picture signal. In either case, the threshold for the differential picture signal must be set at such a low value that a defect caused by typically a very small extraneous material can be detected. In consequence, a false signal representing infinitesimal unevenness of the surface of the substrate 1 serving as an object of inspection is also detected inadvertently.

In order to solve the problem caused by the fact that a defect candidate signal represented by the binary picture signal includes false information as described above, the defect-candidate-characteristic-quantity extracting circuit 405 is employed for extracting characteristic quantities of the detected defect candidate points from the binary picture signal and/or the digital detected picture signal output by the AD conversion circuit 402 at the detected defect candidate points. As described above, examples of the characteristic quantities of a defect candidate point are the area, the coordinate position, the maximum length and the moment of the defect candidate. By the maximum length, projection lengths in the x-axis and y-axis directions are meant. Then, the defect determining circuit 406 determines that a defect candidate point is a real defect if the characteristic quantities of the defect candidate point output by the defect-candidate-characteristic-quantity extracting circuit 405 exceed predetermined criteria.

As described above, the signal processing system 401 is capable of inspecting an object by detection of a signal generated by a defect caused by typically a very small extraneous material with a size of about 0.1 $\mu$m or smaller by discriminating a false-information signal.

Figure 10:
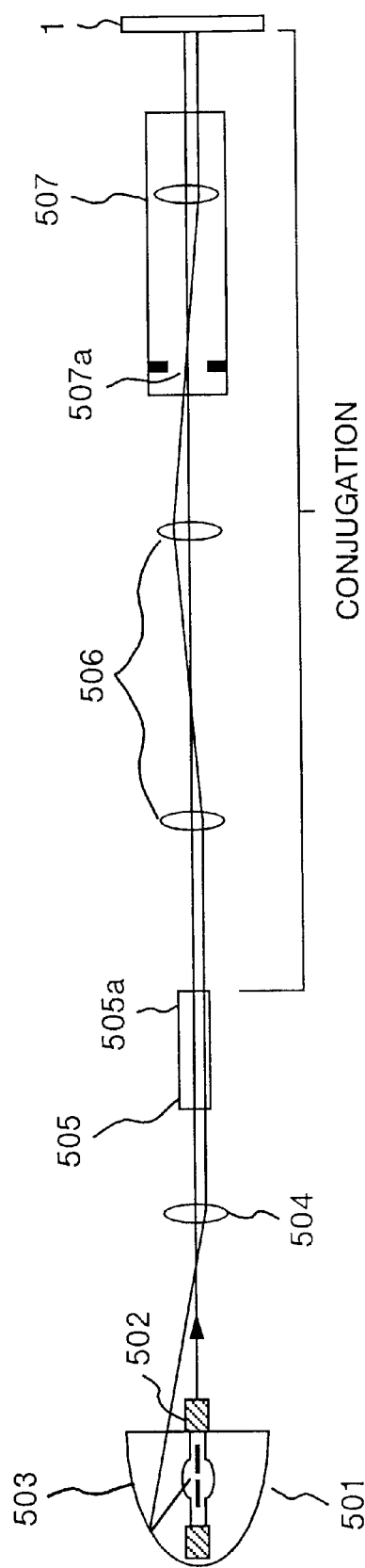
FIG. 10 is a diagram showing the configuration of another embodiment implementing the radiation optical system employed in the first embodiment implementing the defect inspecting apparatus shown in FIG. 1.
Figure 11:
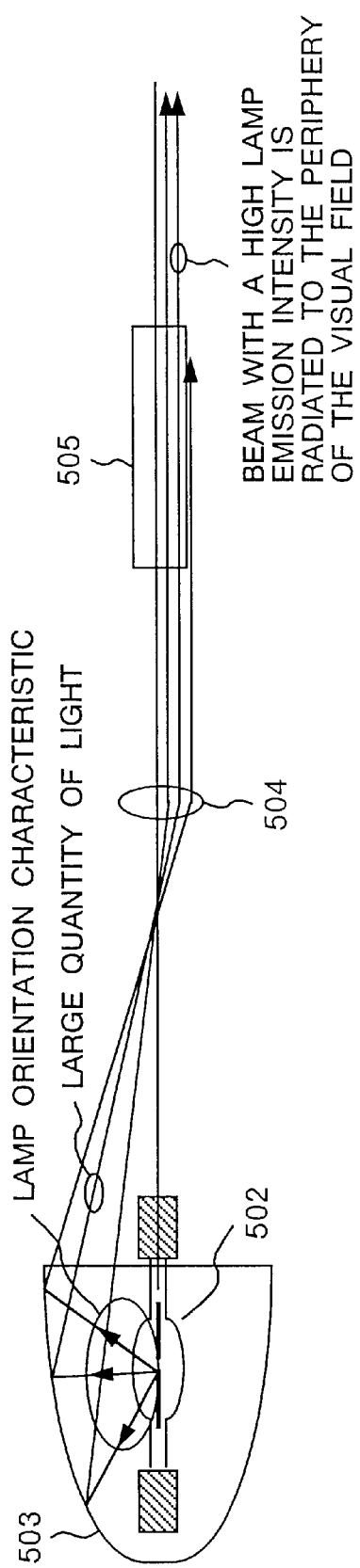
FIG. 11 is an explanatory diagram showing a case in which the illumination intensity on the periphery of an area of detection is increased by using the radiation optical system shown in FIG. 10 to effectively utilize the light quantity of a beam emitted by a lamp serving as a light source and make use of the orientability of the beam emitted by the lamp serving as a light source.

The following description explains an embodiment different from the embodiments described above by referring to FIGS. 10 and 11. This embodiment implements a radiation optical system employed in the defect inspecting apparatus provided by the present invention. As shown in FIG. 11, the embodiment implementing the radiation optical system includes: an illumination light source 501 comprising a filament light source 502 implemented by typically a halogen lamp and an elliptical mirror 503 for converging a light emitted by the filament light source 502, a collimator lens 504 for converting the light emitted and converged by the illumination light source 501 into all but parallel lights, a rod lens (glass bar) 505 serving as a secondary light source at an emitting end 505a thereof for emitting a spot beam by transmission of the all but parallel lights generated as a result of conversion by the collimator lens 504 through the rod lens 505, a pair of Fourier transformation lenses 506 for converging the spot beam emitted by the emitting end 505a serving as the secondary light source on an eye 507a of an objective lens 507, and the objective lens 507.

Figure 12:
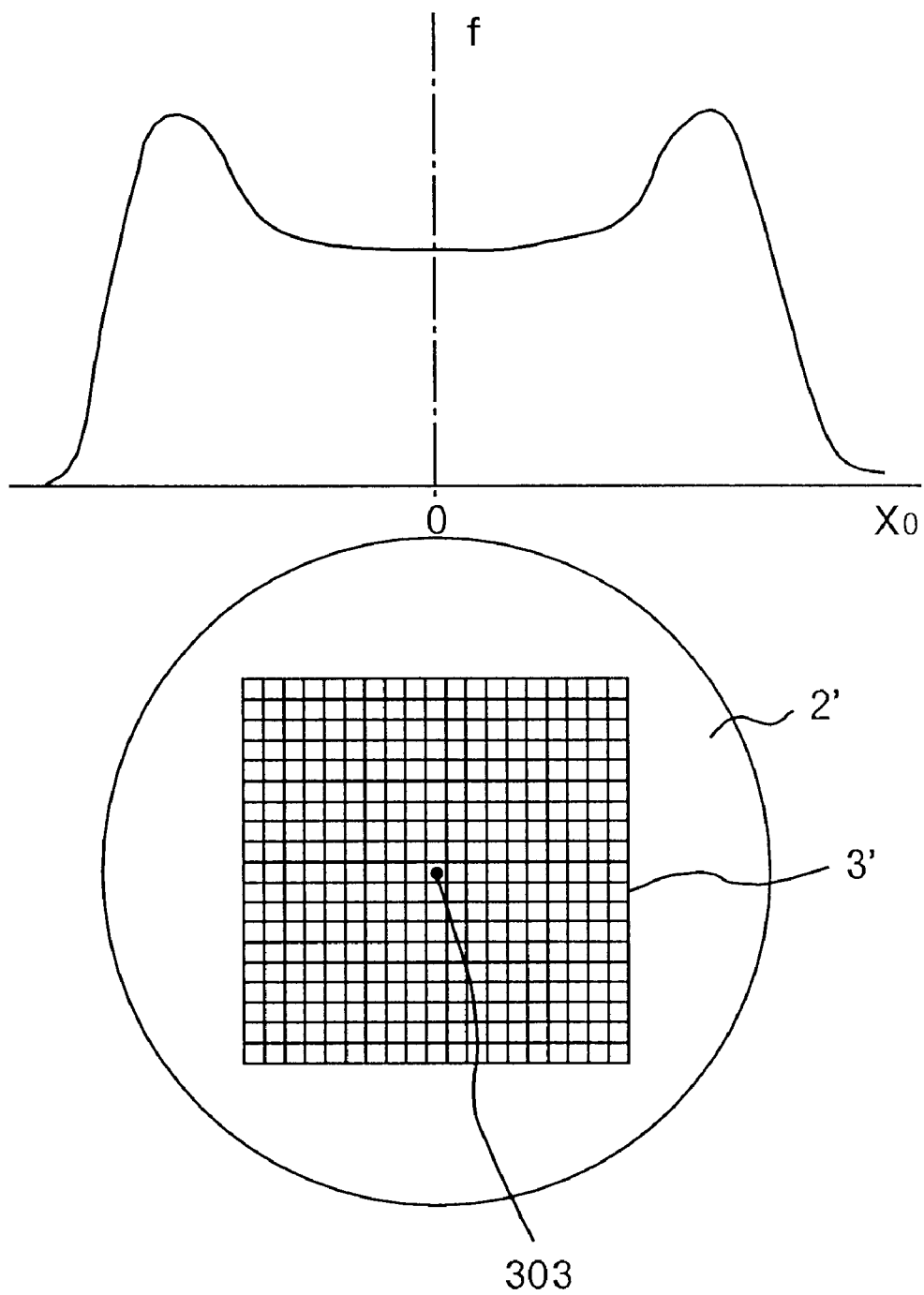
FIG. 12 is a diagram showing an illumination distribution over an area of detection obtained by using the radiation optical system shown in FIGS. 10 and 11.

It should be noted that the emitting end 505a of the rod lens 505 and the surface of the substrate 1 serving as an object of inspection are designed into a configuration wherein the two elements are in an optically conjugate relation. By the way, by making use of the orientation characteristic of the lamp 502 shown in FIG. 11, a beam emitted by the lamp 502 at a high emission intensity can be radiated to the periphery of an area of detection 3' which is also the periphery of an area of illumination 2' as shown in FIG. 12. As a result, it is possible to increase the quantity of light on the periphery of the area of detection 3' which is also referred to as a detection visual field. In this case, since a filament lamp is used as the light source 502, the quantity of a light emitted by the lamp light source 502 can be effectively utilized without reducing the quantity of light. In addition, in the case of this illumination optical system, it is possible to illuminate the area of detection 3' with an illumination distribution shown in FIG. 12 as a solution to a problem caused by the fact that, the farther the distance from a location to the optical axis on the objective lens 507, the lower the MTF at that location. It should be noted that illumination with a distribution like the one shown in FIG. 12 is referred to as pseudo zonal illumination with an increased illumination intensity on the periphery.

It is worth noting that, by placing a cylindrical lens 105 inside, before or after a Fourier transformation lens 506, it is possible to obtain the beam 107 with a slit shape explained earlier in the description of the first embodiment implementing a defect inspecting apparatus. In addition, the illumination intensity at the periphery of the area of detection 3 can also be increased as well. As a result, the detection optical system 301 is capable of increasing the intensity of a light which is scattered or diffracted by a defect caused by typically an extraneous material and then received by a pixel on the periphery of the detector 302 with a smallest MTF, making it possible to detect also a defect caused by typically a very small extraneous material with a size of about 0.1 $\mu$m or smaller in the area of detection with a high degree of sensitivity and at a high speed.

As described above, according to the present invention, it is possible to increase the illumination at the periphery of the area of detection by a detector such as a TDI image sensor and, hence, to increase illumination efficiency as a solution to a problem caused by the fact that, the farther the distance from a location to the optical axis in the detection optical system, the lower the MTF at that location. Thus, there is exhibited an effect that it is possible to detect also a defect caused by typically a very small extraneous material with a size in a range of about 0.1 $\mu$m to about 0.5 $\mu$m in an area of detection on a substrate serving as an object of inspection such as an LSI wafer or even a defect caused by typically a very small extraneous material with a size smaller than 0.1 $\mu$m in the area of detection with a high degree of sensitivity and at a high speed, that is, at a high throughput by using a low-cost light source.

In addition, according to a configuration described above, an optical image based on a DUV (Distant Ultra Violet) laser beam such as an excima laser obtained from a substrate serving as an object of inspection can be received by a TDI image sensor, making it possible to detect also a defect caused by typically a very small extraneous material with a size in a range of about 0.1 μm to about 0.5μm or even a defect caused by typically a very small extraneous material with a size smaller than 0.1 μm.

Furthermore, according to a configuration described above, a problem of an insufficient illumination intensity on the periphery of an area of detection on a substrate serving as an object of inspection caused by the fact that, the farther the distance from a region to the optical axis of the detection optical system, the lower the MTF for the region, is solved by effectively utilizing the light quantity of a beam emitted by a lamp serving as a light source, making it possible to detect also a defect caused by typically a very small extraneous material with a size smaller than 0.1 μm in the area of detection with a high degree of sensitivity and at a high speed.

What is claimed is:

1. A defect inspection method comprising the steps of:
   radiating a Gaussian light beam to an area of detection on a substrate serving as an object of inspection and having a circuit pattern created thereon by using a radiation optical system wherein said Gaussian light beam is shaped to give an illumination-intensity distribution of a Gaussian distribution having a standard deviation about equal to a distance from an optical axis of said area of detection to peripheries of said area of detection;
   forming an optical image of said area of detection on said substrate serving as an object of inspection by radiating of said shaped Gaussian light beam to a photo-sensitive surface of a detector corresponding to said area of detection and detecting a picture signal corresponding to said area of detection and originating from said detector; and
   processing so as to judge whether or not a defect exists in said area of detection on the basis of said detected picture signal originating from said detector by a signal processing system.

2. A defect inspection method according to claim 1 wherein said shaped Gaussian light beam has a slit shape; and
   said substrate is moved relatively to said Gaussian light beam having said slit shape in a direction crossing a longitudinal direction of said slit shape of the Gaussian light beam.

3. A defect inspection method according to claim 2 wherein said detector is a TDI image sensor.

4. A defect inspection method according to claim 2, wherein said shaped Gaussian light beam is formed by a DUV-light beam and said detector is a TDI image sensor having sensitivity for said DUV-light.

5. A defect inspection method according to claim 4, wherein said TDI image sensor is formed by a back-surface-radiation TDI image sensor which receives an incident light impinging on a rear side of a thin Si substrate.

6. A defect inspection method according to claim 1 wherein said shaped Gaussian light beam is radiated to the area of detection on said substrate from a direction with respect to the optical axis.

7. A defect inspection method according to claim 1, wherein said defect is a defect caused by an extraneous material.

8. A defect inspection method according to claim 1, wherein said shaped Gaussian light beam is formed by a DUV-light beam.

9. A defect inspection method comprising the steps of:
   radiating a Gaussian light beam to an area of detection on a substrate serving as an object of inspection and having a circuit pattern created thereon by using a radiation optical system wherein said Gaussian light beam is shaped to give an illumination-intensity distribution of a Gaussian distribution having a ratio of illumination-intensities on said peripheries of said area of detection to an illumination-intensity on an optical axis of said area of detection which is in a range of 0.46 to 0.73;
   forming an optical image of said:area of detection on said substrate serving as an object of inspection by radiation of said shaped Gaussian light beam to a photo-sensitive surface of a detector corresponding to said area of detection and detecting a picture signal corresponding to said area of detection and originating from said detector by using a detection optical system; and
   processing so as to judge whether or not a defect exists in said area of detection on the basis of said detected picture signal originating from said detector by a signal processing system.

10. A defect inspecting apparatus comprising:
    a radiation optical system for radiating a Gaussian light beam to an area of detection on a substrate serving as an object of inspection and having a circuit pattern created thereon wherein said Gaussian light beam is shaped to give an illuminatio-intensity distribution of a Gaussian distribution having a standard deviation about equal to a distance from an optical axis of said area of detection to peripheries of said area of detection;
    a detection optical system for forming an optical image of said area of detection on said substrate by radiation of said shaped Gaussian light beam to a photo-sensitive surface of a detector corresponding to said area of detection and for detecting a picture signal corresponding to said area of detection and originating from said detector; and
    a signal processing system for forming a judgment as to whether or not a defect exists in said area of detection on the basis of a detected picture signal originating from said detector employed in said detection optical system.

11. A defect inspecting apparatus according to claim 10 wherein said radiation optical system is provided on an optical system which forms said shaped Gaussian beam in a state of a slit shape; and further comprising a stage movement unit for moving relatively a stage mounted said substrate to said Gaussian beam in a direction crossing a longitudinal direction of said slit shape of the Gaussian light beam.

12. A defect inspecting apparatus according to claim 11 wherein said detector is a TDI image sensor.

13. A defect inspecting apparatus according to claim 11, wherein said radiation optical system is provided a DUV-light source for irradiating a DUV-light beam and said detector in said detection optical system is formed by TDI image sensor having sensitivity for said DUV-light.

14. A defect inspecting apparatus according to claim 13, wherein said TDI image sensor is formed by a back-surface-radiation TDI image sensor which receives an incident light impinging on a rear side of a thin Si substrate.

15. A defect inspecting apparatus according to claim 10 wherein said radiation optical system is provided on an optical system for radiating said shaped Gaussian beam to the area of detection on said substrate from a direction with respect to the optical axis.

16. A defect inspecting apparatus according to claim 10, wherein said defect is a defect caused by extraneous material.

17. A defect inspecting apparatus according to claim 10, wherein said radiation optical system is provided a DUV-light source-for irradiating a DUV-light beam.

18. A defect inspecting apparatus comprising:

a radiation optical system for radiating a Gaussian light beam to an area of detection on a substrate serving as an object of inspection and having a circuit pattern created thereon wherein said Gaussian light beam is shaped to give an illumination-intensity distribution of a Gaussian distribution having a ratio of illumination-intensities on said peripheries of said area of detection to an illumination-intensity on an optical axis of said area of detection which is in a range of 0.46 to 0.73;

a detection optical system for forming an optical image of said area of detection on said substrate by radiation of said shaped Gaussian light beam to a photo-sensitive surface of a detector corresponding to said area of detection and for detecting a picture signal corresponding to said area of detection and originating from said detector; and a signal processing system for forming a judgment as to whether or not a defect exists in said area of detection on the basis of a detected picture signal originating from said detector employed in said detection optical system.

19. A defect inspecting apparatus comprising:

a radiation optical system for radiate a Gaussian light beam to an area of detection on a substrate serving as an object of inspection and having a circuit pattern created thereon wherein said Gaussian light beam is shaped by adaptation of the diameter or the longitudinal length of said beam to the distance between peripheries having the optical axis of said area of detection as the center thereof so that the ratio of an illumination intensity on said peripheries of said area of detection to an illumination intensity at the center of said area of detection is in a range of 0.46 to 0.73;

a detection optical system for forming an optical image of said area of detection on said substrate serving as an object of inspection by radiation of said shaped Gaussian light beam to a photo-sensitive surface of a detector corresponding to said area of detection and for detecting a picture signal corresponding to said area of detection and originating from said detector; and a signal processing system for forming a judgment as to whether or not a defect exists in said area of detection on the basis of a detected picture signal originating from said detector employed in said detection optical system.

20. A defect inspecting apparatus according to claim 19, wherein said defect is a defect caused by extraneous material.

* * * * *